US007402819B2

(12) United States Patent  
Saracen

(10) Patent No.: US 7,402,819 B2  
(45) Date of Patent: Jul. 22, 2008

(54) RESPIRATION PHANTOM FOR QUALITY ASSURANCE

(75) Inventor: Michael J. Saracen, Oakland, CA (US)

(73) Assignee: Accuray Incorporated, Sunnyvale, CA (US)

( * ) Notice: Subject to any disclaimer, the term of this patent is extended or adjusted under 35 U.S.C. 154(b) by 245 days.

(21) Appl. No.: 11/293,458

(22) Filed: Dec. 1, 2005

(65) Prior Publication Data

US 2007/0140413 A1 Jun. 21, 2007

(51) Int. Cl.
*A61N 5/00* (2006.01)
*G21G 5/00* (2006.01)

(52) U.S. Cl. ............. 250/492.1; 250/484.4; 250/252.1; 250/583; 250/585; 600/1; 600/3; 438/48; 378/65; 378/158; 378/205

(58) Field of Classification Search ............. 250/492.1, 250/484.4, 252.1, 583, 585; 600/1, 3; 438/48; 378/65, 158, 205
See application file for complete search history.

(56) References Cited

U.S. PATENT DOCUMENTS

| 1,252,550 | A | 1/1918 | Champney | |
|---|---|---|---|---|
| 6,528,803 | B1 | 3/2003 | Ritt | |
| 6,675,116 | B1 | 1/2004 | Ritt | |
| 7,151,253 | B2 * | 12/2006 | Varchena et al. | 250/252.1 |
| 2003/0220718 | A1 * | 11/2003 | Jaszczak et al. | 700/282 |
| 2007/0071176 | A1 | 3/2007 | Main et al. | |

OTHER PUBLICATIONS

"Rando Phantom", The Phantom Laboratory, New York http://www.phantomlab.com/rando.html, Aug. 2004.*
"RANDO Phantom" The Phantom Laboratory, New York http://www.phantomlab.com/rando.html
PCT International Search Report, PCT/US06/46119, Filed Date Nov. 30, 2006, mailed Dec. 14, 2007.
PCT Written Opinion of the International Searching Authority, PCT/US06/46119, Filed Date Nov. 30, 2006, mailed Dec. 14, 2007.
"Anthropomorphic Phantoms," Radiological Physics Center. Retrieved from http://rpc.mdanderson.org/rpc/services/Anthropomorphic_%20Phantoms/Anth_SRS.htm (Retrieved on Mar. 28, 2007).
"Instructions for SRS Quality Audit System," Radiological Physics Center. Retrieved from http://rpc.mdanderson.org/rpc/services/Anthropomorphic_%20Phantoms/SRSInstrucForInst.pdf (Retrieved on Mar. 28, 2007).
Yu, Cheng Ph.D. et al., "An Anthropomorphic Phantom Study of the Accuracy of CyberKnife Spinal Radiosurgery," Neurosurgery, vol. 55, No. 5, Nov. 2004, pp. 1138-1149.

(Continued)

*Primary Examiner*—Jack Berman
*Assistant Examiner*—Meenakshi S Sahu
(74) *Attorney, Agent, or Firm*—Blakely, Sokoloff, Taylor & Zafman LLP

(57) ABSTRACT

A respiration phantom that may be used to perform quality assurance on a radiation delivery system. The respiration phantom includes a human-like skeletal structure, at least one deformable component, and a respiration actuator. The deformable component is positionable at least partially internal to the human-like skeletal structure, has a shape resembling an organ of a human anatomy, and attenuates radiation substantially similarly to the organ of the human anatomy. The respiration actuator is positioned to deform the deformable component with a respiration-like motion.

33 Claims, 7 Drawing Sheets

OTHER PUBLICATIONS

U.S. Appl. No. 11/273,711, filed Nov. 14, 2005, Main et al., "Unified Quality Assurance for a Radiation Treatment Delivery System".

"Dynamic Phantom," CIRS Model 008 Dynamic Thorax Phantom Specifications, pp. 53-54.

* cited by examiner

RESPIRATION PHANTOM FOR QUALITY ASSURANCE

TECHNICAL FIELD

This disclosure relates generally to quality assurance for radiation delivery systems, and in particular but not exclusively, relates to a respiration phantom.

BACKGROUND

In radiosurgery or radiotherapy (collectively referred to as radiation treatment) very intense and precisely collimated doses of radiation are delivered to a target region in the body of a patient in order to treat or destroy lesions. Typically, the target region is composed of a volume of tumorous tissue. Radiation treatment requires an extremely accurate spatial localization of the targeted lesions. As a first step in performing radiation treatment, it is necessary to determine with great precision the location of a lesion and any surrounding critical structures, relative to the reference frame of the treatment device. Computed tomography ("CT"), magnetic resonance imaging ("MRI") scans, and other imaging modalities enable practitioners to precisely locate a lesion relative to skeletal landmarks or implanted fiducial markers. However, it is also necessary to control the position of the radiation source so that its beam can be precisely directed to the target tissue while avoiding adjacent critical body structures.

Thus radiation treatment necessitates high precision diagnosis and high precision radiation source control. The consequences of deviating outside the prescribed tolerances for the diagnosis and the radiation source control can be potentially devastating to a patient. Accordingly, quality assurance mechanisms should be implemented to ensure proper alignment and configuration of the radiation delivery system prior to delivering a prescribed radiation dose to a patient.

Conventional quality assurance mechanisms include pointing the radiation source at an alignment marker, delivering a radiation dose to the alignment marker, and then analyzing the alignment marker itself to determine if the prescribed dose was actually delivered to the correct location. If the prescribed dose was delivered as expected, then the radiation treatment delivery system is deemed properly aligned. If the prescribed dose was not delivered as expected, then the radiation treatment delivery system is deemed misaligned.

Conventional alignment markers include silver loaded gels capsules or photographic film canisters that can store readable information about the distribution of the radiation dose delivered to the alignment marker. However, these alignment markers are static objects that neither resemble an actual patient nor move as a patient would due to breathing. As such, prior art alignment markers do not adequately recreate the actual conditions that exist during delivery of a prescribed dose of radiation to a living patient.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Embodiments of a system and method for respiration phantom for quality assurance testing of a radiation delivery system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
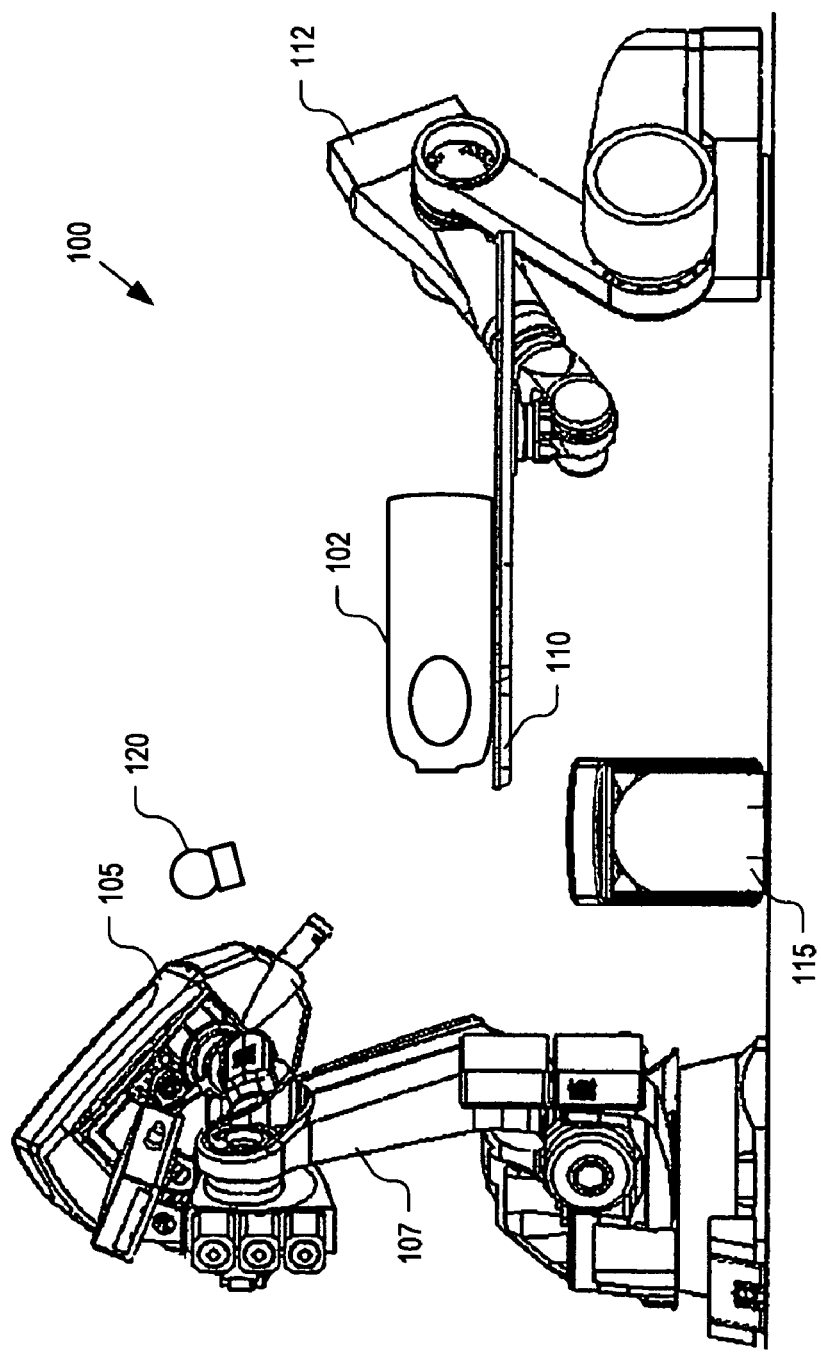
FIG. 1 is diagram illustrating execution of a quality assurance test procedure on a radiation delivery system using a respiration phantom, in accordance with an embodiment of the invention.

FIG. 1 is diagram illustrating execution of a quality assurance ("QA") test procedure on a radiation delivery system 100 using a respiration phantom 102, in accordance with an embodiment of the invention. The illustrated embodiment of radiation delivery system 100 includes a radiation source 105, a source positioning system 107, a treatment couch 110, a couch positioning system 112 (also referred to as a patient positioning system), imaging detectors 115 (also referred to as imagers, only one is illustrated), and imaging sources 120 (only one is illustrated).

Radiation delivery system 100 may be used to perform radiotherapy or radiosurgery to treat or destroy lesions within a patient. During radiation treatment, the patient rests on treatment couch 110, which is maneuvered to position the lesion or volume of interest ("VOI") to a preset position or within an operating range accessible to radiation source 105 (e.g., field of view). Similarly, radiation source 105 is maneuvered with multiple degrees of freedom (e.g., rotational and translational freedom) to one or more locations during delivery of a treatment plan. At each location, radiation source 105 delivers a dose of radiation as prescribed by the treatment plan.

In one embodiment, radiation delivery system 100 is an image guided radiation treatment delivery system. Together, imaging sources 120 and imaging detectors 115 form an image guidance system that provides visual control over the position of treatment couch 110 and the patient thereon. In one embodiment, couch positioning system 112 receives feedback from the image guidance system to provide accurate control over both the displacement and orientation of the VOI within the patient. In one embodiment, visual feedback from the image guidance system is further used by source positioning system 107 to position, align, and track the target VOI within the patient.

Prior to delivery of a treatment plan to a patient, QA mechanisms may be executed to ensure radiation delivery system 100 is properly aligned, configured, and capable of delivering the treatment plan as prescribed. These QA mechanisms, also referred to as confidence checks, validate that the image guidance system, couch positioning system 112, source positioning system 107, and radiation source 105, itself, are all calibrated and aligned with each other and delivering a treatment plan as desired. If anyone of these subsystems is misaligned with one or more other subsystems, a treatment plan could be erroneously delivered to a patient's detriment.

Respiration phantom 102 is an anthropomorphic QA marker that dynamically moves with a respiration-like motion. To implement a QA test, a dose of radiation can be delivered to respiration phantom 102 while it is caused to move with the respiration-like motion. Subsequently, respiration phantom 102 may be analyzed to determine whether the dose of radiation was delivered as expected. Since respiration phantom 102 simulates human-like breathing, it is capable of testing the ability of radiation delivery system 100 to track a VOI within a patient that is moving due to natural breathing. In one embodiment, respiration phantom 102 is fabricated of components that image (e.g., x-ray image, ultrasound image, CT image, MR image, etc.) substantially similar to the human anatomy. Since respiration phantom 102 is anthropomorphic (e.g., includes human-like skeletal structure and major internal organs), respiration phantom 102 tests the ability of the image guidance system to identify human features, lock onto these features, and even track these features while moving due to respiration. In one embodiment, the internal organ-like and skeletal-like components of respiration phantom 102 are fabricated of materials that attenuate radiation in a similar manner to their living counterparts (e.g., water equivalent attenuation). As such, respiration phantom 102 can be used to accurately determine the dose of radiation delivered to a selected VOI and the amount of radiation exposure to the surrounding organs and skeletal structures.

Figure 2:
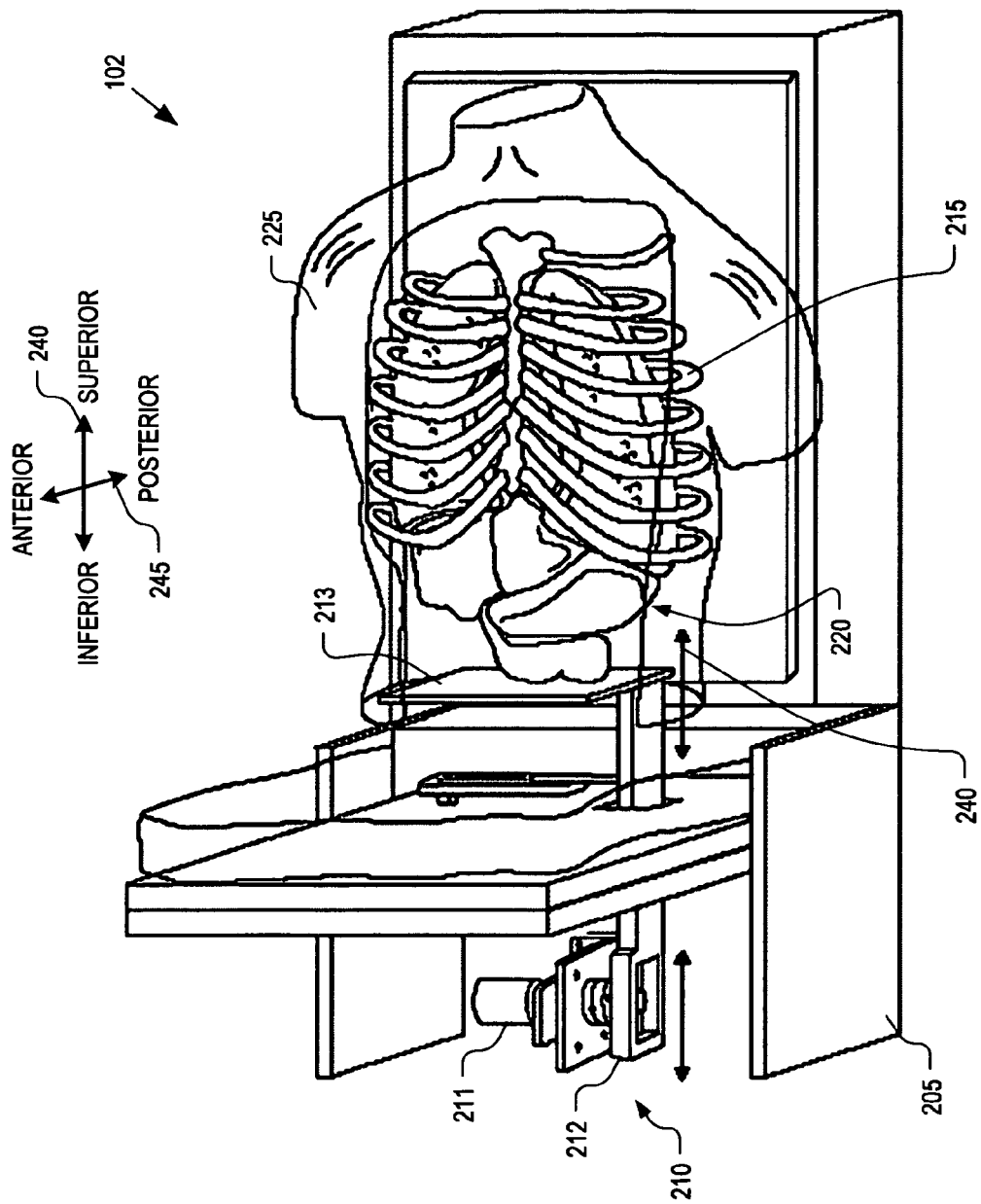
FIG. 2 is a perspective view of a respiration phantom, in accordance with an embodiment of the invention.

FIG. 2 is a perspective view of respiration phantom 102, in accordance with an embodiment of the invention. The illustrated embodiment of respiration phantom 102 includes a base 205, a respiration actuator 210, a human-like skeletal structure 215, organ components 220, and a skin-like sheath 225. Respiration phantom 102 is an anthropomorphic QA phantom that resembles the middle portion of the human anatomy between the waist and neck.

In one embodiment, human-like skeletal structure 215 includes a rib cage, a sternum, and a spin. However, other embodiments of human-like skeletal structure 215 may include more or fewer human-like bone structures. For example, human-like skeletal structure 215 may further include a pelvic bone or exclude the spinal cord. Human-like skeletal structure 215 may be fabricated of materials having similar x-ray imaging qualities (or other imaging modalities) and radiation attenuation properties as the corresponding human skeletal structures. For example, human-like skeletal structure 215 may be fabricated of barium infused hardened foam, such as fabricated by Sawbones, A Division of Pacific Research Laboratories, Inc. of Vashon, Wash.

Figure 3:
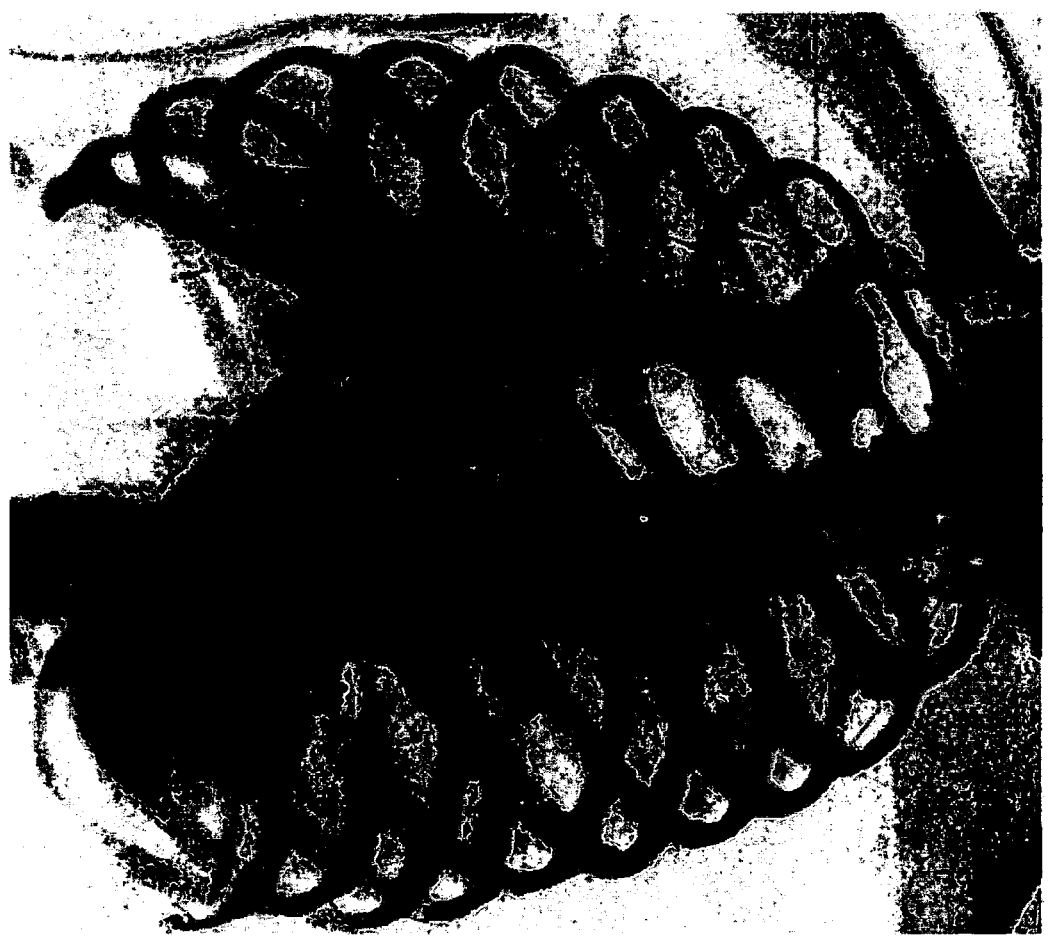
FIG. 3 is an x-ray image of a respiration phantom illustrating a human-like skeletal structure, in accordance with an embodiment of the invention.

FIG. 3 is a representative x-ray image of respiration phantom 102 illustrating human-like skeletal structure 215, in accordance with an embodiment of the invention. As illustrated, the individual bone structures of human-like skeletal structure 215 are radiographically distinct and image similar to a real human skeleton. The radiographical distinctness of human-like skeletal structure 215 enables visual tracking via image registration using the imaging system of radiation delivery system 100.

Returning to FIG. 2, respiration phantom 102 includes a plurality of organ components 220 internal to human-like skeletal structure 215. Organ components 220 each have a shape resembling a different organ of the human anatomy. In one embodiment, each one of organ components 220 is fabricated of materials having similar x-ray imaging qualities (or other imaging modalities) and radiation attenuation properties as the corresponding human organs. For example, organ components 220 may be fabricated of foam or plastic.

In one embodiment, each organ component 220 is removable from respiration phantom 102 and replaceable with a similarly shaped gel organ. The gel organ may be a sack or container having a shape of the corresponding organ and filled with a radiologically sensitive gel (e.g., BANG® polymer gel by MGS Research, Inc. of Madison, Conn.). If it is desired to determine the exposure a particular organ of a patient will received during delivery of a treatment plan, then the corresponding organ component 220 (and possibly the surrounding organ components 220) can be replaced with a gel organ filled with the radiologically sensitive gel. After the treatment plan is delivered, the gel organs are removed and analyzed to determine the dose delivered to the intended VOI and the exposure to surrounding tissue, organs, or bones. Since respiration phantom 102 is anthropomorphic, and organ components 220, human-like skeletal structure 215, and skin-like sheath 225 are all fabricated to attenuate radiation in a similar manner to the corresponding human structures, respiration phantom 102 provides a realistic simulation of the actual three dimensional dose delivery and exposure distribution.

Figure 4:
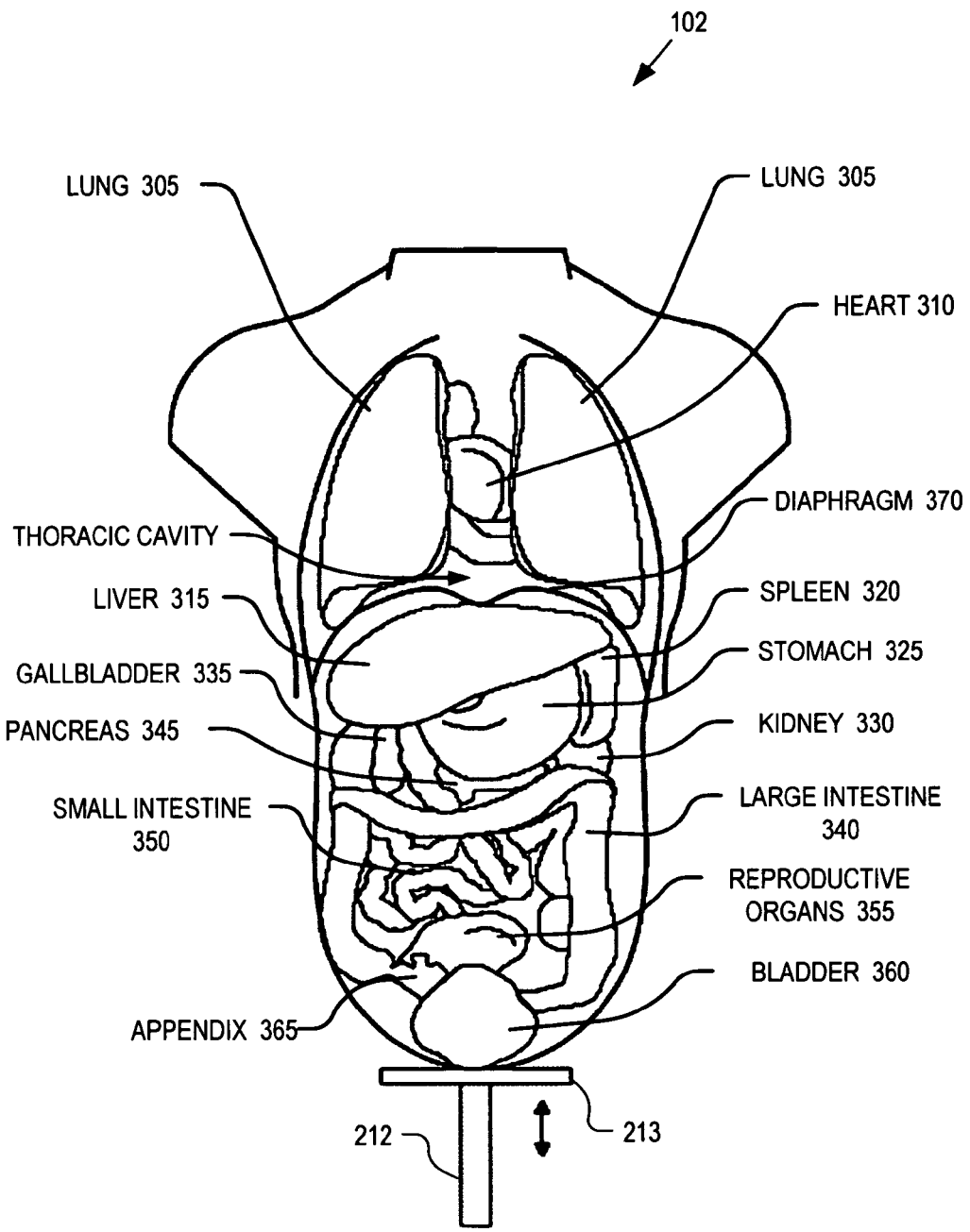
FIG. 4 is a diagram illustrating component organs of a respiration phantom that are removable and replaceable with deformable component organs, in accordance with an embodiment of the invention.

FIG. 4 is a diagram illustrating example component organs 220 of respiration phantom 102 that are removable and replaceable with gel organs, in accordance with an embodiment of the invention. The illustrated embodiment of respiration phantom 102 includes lung components 305, a heart component 310, a liver component 315, a spleen component 320, a stomach component 325, kidney components 330, a gallbladder component 335, a large intestine component 340, a pancreas component 345, a small intestine component 350, reproductive organ components 355, a bladder component 360, and an appendix component 365.

It should be appreciated that component organs 220 illustrated in FIG. 4 are merely representative of possible organs that may be included within respiration phantom 102. However, other organs not illustrated may be included while some components illustrated may be excluded. For example, one embodiment of respiration phantom 102 excludes large intestine component 340, small intestine component 350, reproductive organ components 355, bladder component 360, and appendix component 365.

Returning to FIG. 2, respiration phantom 102 includes respiration actuator 210 to impart a respiration-like motion on component organs 220, human-like skeletal structure 215, and skin-like sheath 225. In the illustrated embodiment, respiration actuator 210 includes a motor 211 coupled to a push rod 212 and push plate 213 to reciprocally compress component organs 220 along an inferior to superior axis 240. The motorized components (e.g., push rod 212 and push plate 213) that are in the anatomical field of view may be fabricated of radiolucent materials (e.g., plastic). In one embodiment, component organs 220 are deformable. By compressing component organs 220 along inferior to superior axis 240, component organs 220 simultaneously expand or bulge along a posterior to anterior axis 245. When component organs 220 expand along axis 245, they press against the rib cage of human-like skeletal structure 215 creating a human-like sinusoidal breathing motion. The rate of reciprocal compression may be adjusted to simulate at rest breathing, high activity breathing, or anywhere in between.

Human breathing is created by a diaphragm that simultaneously pushes down on component organs 220 (axis 240) located in the abdominopelvic cavity to draw air into lungs 305 causing the thoracic cavity to expand outwards (axis 245). The respiration motion generated by the embodiment of respiration actuator 210 pushes component organs 220 upwards causing them to simultaneously bulge outwards. While the directions of motion are reversed, respiration actuator 210 illustrated in FIG. 2 replicates simultaneous motions along axes 240 and 245. Accordingly, if a VOI is located on one of lungs 305, then the VOI will experience an inferior to superior motion, as well as, a simultaneous posterior to anterior motion. Generating simultaneous motion along both axes 240 and 245 provides a mechanism to fully test the visual tracking capabilities of radiation delivery system 100.

In one embodiment, respiration actuator 210 includes a programmable control system. The control system can be programmed to change breathing patterns imparted to the component organs 220 to test various different respiration scenarios. For example, pre-recorded breathing data from a living patient can be imported into the control system so that respiration actuator 210 can simulate the breathing motion. The pre-recorded breathing data could be data collected during a previous treatment and then imported into the control system to recreate or simulate the respiration-like motion of a particular VOI under similar conditions.

FIG. 2 illustrates only one of many possible configurations for respiration actuator 210. For example, in the illustrated embodiment, respiration actuator 210 is illustrated with a mechanical motor 211; however, respiration actuator 210 may be implemented with a pneumatic cylinder as well. In one embodiment, push rod 212 of respiration actuator 210 may couple to the sternum of the rib cage to transfer the upward pushing force thereon. In one embodiment, respiration phantom 102 may include a diaphragm member (e.g., diaphragm 370 illustrated in FIG. 4) located below lungs 305 and above liver 315. In this embodiment, push rod 212 may push directly on the diaphragm member. Furthermore, respiration phantom 102 may include a thoracic cavity and an abdominopelvic cavity separated by the diaphragm member. In this diaphragm member embodiment, respiration actuator 210 may comprise a pump to force the diaphragm member up and down using air pressure. In yet another embodiment, the thoracic cavity and/or the abdominopelvic cavity may be liquid filled and respiration actuator 210 may use hydraulic pressure to impart the respiration-like motion.

Respiration phantom 102 may further include skin-like sheath 225 pulled tight over human-like skeletal structure 215. Skin-like sheath 225 may have a slit down the center of the pelvic region and/or sternum to facilitate removal of component organs 220. Skin-like sheath 225 may be formed of rubber, plastic, silicon, or other pliable materials. The material used to fabricate may be selected for its radiation attenuation properties, such that it attenuates radiation in a manner similar to human skin.

In one embodiment, respiration phantom 102 may include radiation sensors embedded within the individual component organs 220 or strategically positioned in a grid like fashion throughout the body cavity for measuring radiation exposure. For example, the radiation sensors may include arrays of metal oxide semiconductor ("MOS") field effect transistors ("FET") sensors, TLD sensors, or the like.

Figure 5:
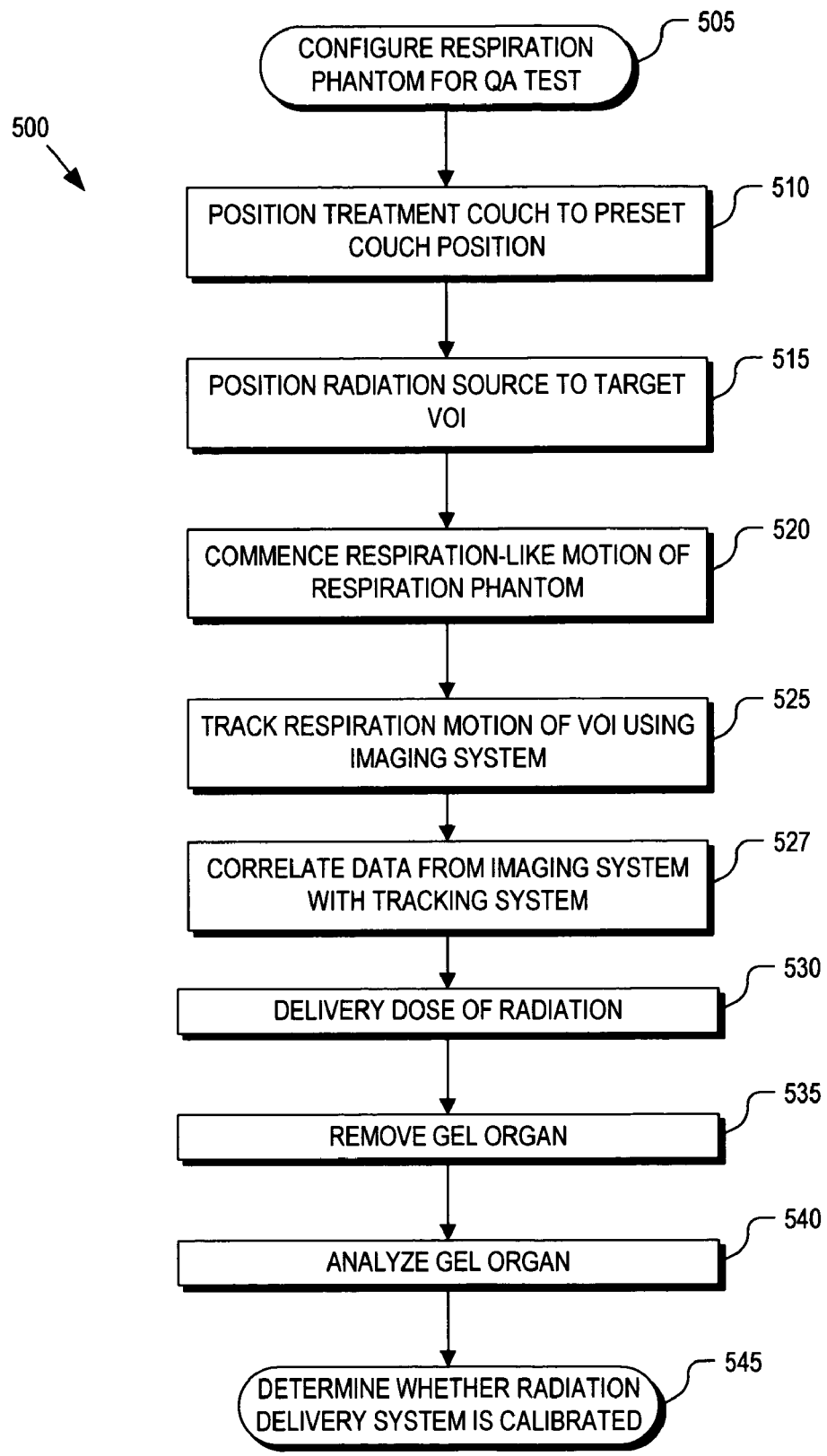
FIG. 5 is a flow chart illustrating a process to implement a quality assurance test procedure on a radiation delivery system using a respiration phantom, in accordance with an embodiment of the invention.

FIG. 5 is a flow chart illustrating a process 500 to implement a QA test procedure on radiation delivery system 100 using respiration phantom 102, in accordance with an embodiment of the invention. The order in which some or all of the process blocks appear in process 500 should not be deemed limiting. Rather, one of ordinary skill in the art having the benefit of the present disclosure will understand that some of the process blocks may be executed in a variety of orders not illustrated.

In a process block 505, respiration phantom 102 is configured for the QA test. If it is desired to test delivery of a treatment plan to a VOI in a particular component organ 220 (e.g., component liver 315), then configuring respiration phantom 102 may include removing the selected component organ 220 (e.g., a foam organ) and replacing it with a radiologically sensitive gel organ having a corresponding size and shape (e.g., gel liver organ). Additionally, the component organs 220 surrounding the target organ with the VOI may also be replaced for measuring their exposure to radiation during delivery of the treatment plan. In an embodiment using electronic radiation sensors (e.g., MOS FET sensors or TLD sensors) respiration phantom 102 may not need configuration or the sensors may be positioned for redistributed within the body cavity or component organs 220. With respiration phantom 102 configured, respiration phantom 102 may be temporarily placed onto treatment couch 110 for execution of the QA testing procedure.

In a process block 510, treatment couch 110 is positioned to a preset target position to place respiration phantom 102 into the field of view or operating envelope of radiation delivery system 100. In the embodiment illustrated in FIG. 1, positioning treatment couch 110 includes instructing couch positioning system 112 to move respiration phantom 102 to the preset target position. Maneuvering treatment couch 110 may include guiding couch positioning system 112 using the image guidance system visually tracking recognizable features of respiration phantom 102. Recognizable features of respiration phantom 102 may include human-like skeletal structure 215 or even tracking fiducials (e.g., metal seeds) implanted into respiration phantom 102.

In a process block 515, radiation source 105 is maneuvered to a source position from which radiation source 105 is able to target the VOI within respiration phantom 102. Maneuvering radiation source 105 to the source position may include instructing source positioning system 107 to translate and rotate radiation source 105 under visual feedback from the image guidance system.

In a process block 520, respiration actuator 210 is turned on to commence respiration-like motion by respiration phantom 102. In a process block 525, the image guidance system locks onto recognizable features of respiration phantom 102 to lock onto the VOI and compensate for the respiration-like motion. If the VOI is within hard tissue (e.g., human-like skeletal structure 215), then human-like skeletal structure 215 itself may be used for tracking purposes. If the VOI is within soft tissues (e.g., one of component organs 220), then tracking fiducials can be embedded within the soft tissue surrounding the VOI and tracked by the image guidance system.

In yet other embodiments, tracking emitters (e.g., light emitting diodes ("LEDs"), ultrasonic emitter, etc.) may be strategically placed on the outer surface of respiration phantom 102 and their motion tracked using one or more motion sensors (e.g., infrared camera, ultrasonic receiver, etc.) mounted around respiration phantom 102 (e.g., on the walls or ceiling of the room housing radiation delivery system 100, on treatment couch 110, or otherwise). The motion sensors can monitor the motion of the tracking emitters and provide real-time feedback for dynamic tracking. The tracking emitters and motion sensors may be used in addition to the above x-ray based image guidance system using human-like skeletal structure 215 and/or the implanted tracking fiducials.

Respiration-like motion data can be collected by a tracking system including the tracking emitters and motion sensors and this motion data correlated with the data collected from the x-ray based imaging system as it simultaneously tracks the internal VOI respiration-like motion (process block 527). The correlation of these data sets can be used to help characterize respiration-like motion of a particular VOI within a living patient based solely on real-time feedback from the tracking emitters mounted to the living patient. In this manner, the x-ray based imaging system is used to precisely track a VOI within respiration phantom 102, correlate this motion to feedback data received from the non-x-ray based tracking system, which would then be used during delivery of a treatment plan to a living patient to reduce exposure of the living patient to the x-ray radiation of the image guidance system. In one embodiment, a Synchrony Respiratory Tracking System from Accuray, Inc. of Sunnyvale, Calif. may be used to implement the tracking emitter and motion sensor based tracking system.

In a process block 530, a dose of radiation is delivered to the respiration phantom 102. Process block 530 may include delivering an entire treatment plan including multiple individual dose deliveries. In one embodiment, the treatment plan may be created prior to delivering the treatment plan by CT scanning (other imaging modalities may also be used) respiration phantom 102 using a breathing protocol to obtain reference images of respiration phantom 102, to isolate the VOI, and to generate a four dimensional (three spatial dimensions plus time) treatment plan that is delivered by radiation delivery system 100 in process block 530.

Once the treatment plan has been delivered, the radiologically sensitive gel organs are removed from respiration phantom 102 (process block 535) and analyzed (process block 540). Exposure to radiation causes the radiologically sensitive gel to change optical density by an amount that is related to its exposure. Accordingly, the gel organs can be optically scanned in three dimensions to generate a three dimensional exposure image. By analyzing the three dimensional exposure image, dose measurements can be extracted to determined whether the treatment plan was delivered as expected and whether radiation delivery system 100 is properly calibrated and aligned (process block 545).

Figure 6:
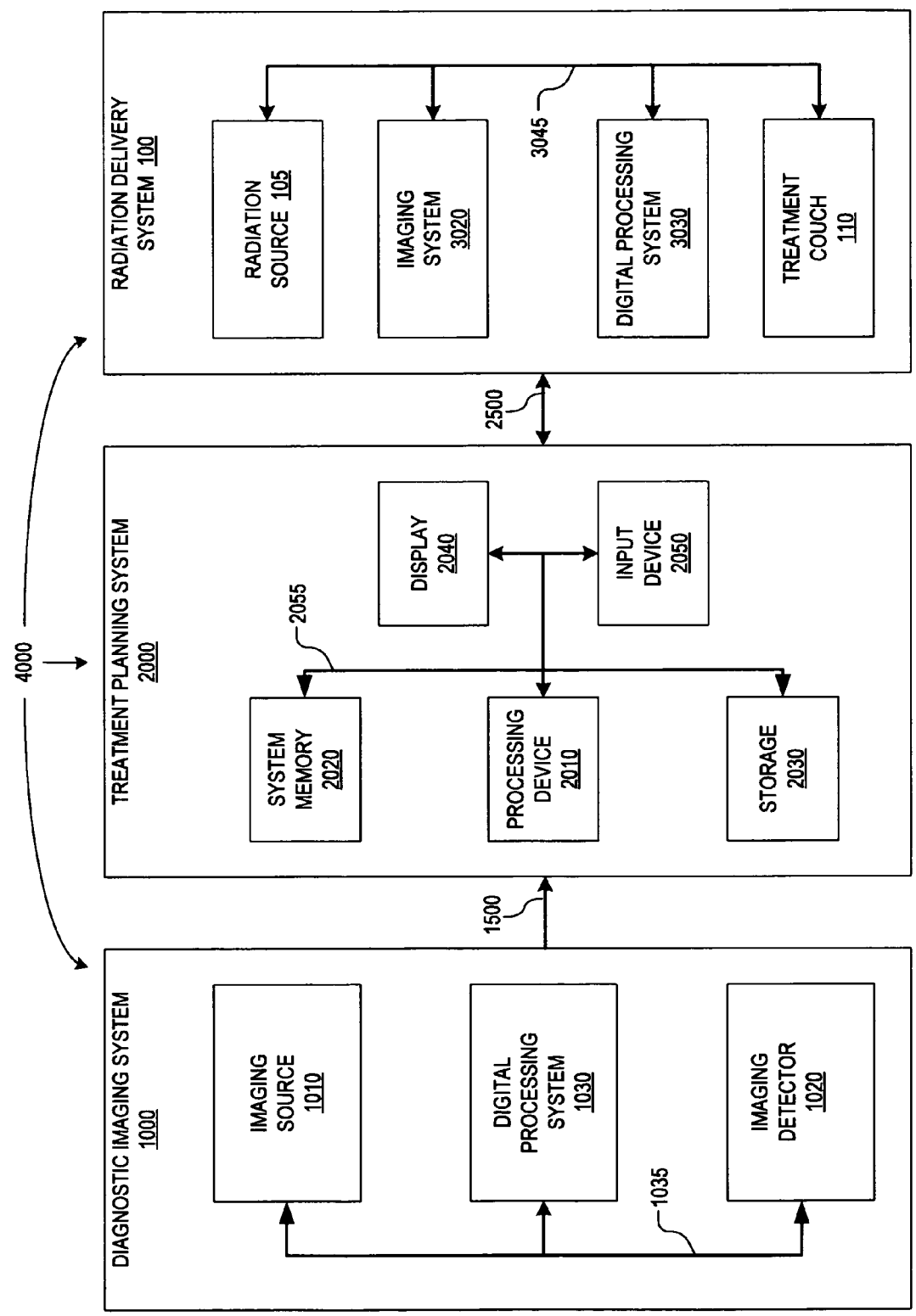
FIG. 6 is a block diagram illustrating a patient treatment system for generating diagnostic images, generating a treatment plan, and delivering the treatment plan, in accordance with an embodiment of the invention.

FIG. 6 is a block diagram illustrating a therapeutic patient treatment system 4000 for generating diagnostic images, generating a treatment plan, and delivering the treatment plan to a patient, in which features of the present invention may be implemented. As described below and illustrated in FIG. 6, systems 4000 may include a diagnostic imaging system 1000, a treatment planning system 2000 and a radiation delivery system 100.

Diagnostic imaging system 1000 may be any system capable of producing medical diagnostic images of the VOI within a patient that may be used for subsequent medical diagnosis, treatment planning and/or treatment delivery. For example, diagnostic imaging system 1000 may be a computed tomography ("CT") system, a magnetic resonance imaging ("MRI") system, a positron emission tomography ("PET") system, an ultrasound system or the like. For ease of discussion, diagnostic imaging system 1000 may be discussed below at times in relation to a CT x-ray imaging modality. However, other imaging modalities such as those above may also be used.

Diagnostic imaging system 1000 includes an imaging source 1010 to generate an imaging beam (e.g., x-rays, ultrasonic waves, radio frequency waves, etc.) and an imaging detector 1020 to detect and receive the beam generated by imaging source 1010, or a secondary beam or emission stimulated by the beam from the imaging source (e.g., in an MRI or PET scan). In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, can also be used that would be illuminated by each x-ray imaging source. Alternatively, other numbers and configurations of imaging sources and imaging detectors may be used.

The imaging source 1010 and the imaging detector 1020 are coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor ("DSP") or other type of device such as a controller or field programmable gate array ("FPGA"). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network ("LAN") link or a wide area network ("WAN") link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a DSP or other type of device such as a controller or FPGA. Processing device 2010 may be configured to execute instructions for performing treatment planning operations discussed herein.

Treatment planning system 2000 may also include system memory 2020 that may include a random access memory ("RAM"), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory ("ROM") and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein.

Processing device 2010 may also be coupled to a display device 2040, such as a cathode ray tube ("CRT") or liquid crystal display ("LCD"), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as radiation delivery system 100, so that it may not be necessary to export from the treatment planning system prior to treatment delivery. Treatment planning system 2000 may be linked to radiation delivery system 100 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or radiation delivery system 100 may be in decentralized locations such that the systems may be physically remote from each other. Alternatively, any of diagnostic imaging system 1000, treatment planning system 2000 and/or radiation delivery system 100 may be integrated with each other in one or more systems.

Radiation delivery system 100 includes a therapeutic and/or surgical radiation source 105 to administer a prescribed radiation dose to a target volume in conformance with a treatment plan. Radiation delivery system 100 may also include an imaging system 3020 (including imaging sources 120 and detectors 115) to capture inter-treatment images of a patient volume (including the target volume) for registration or correlation with the diagnostic images described above in order to position the patient with respect to the radiation source. Radiation delivery system 100 may also include a digital processing system 3030 to control radiation source 105, imaging system 3020, and a patient support device such as a treatment couch 110. Digital processing system 3030 may include one or more general-purpose processors (e.g., a microprocessor), special purpose processor such as a DSP or other type of device such as a controller or FPGA. Digital processing system 3030 may also include other components (not shown) such as memory, storage devices, network adapters and the like. Digital processing system 3030 may be coupled to radiation treatment source 105, imaging system 3020 and treatment couch 110 by a bus 3045 or other type of control and communication interface.

Figure 7:
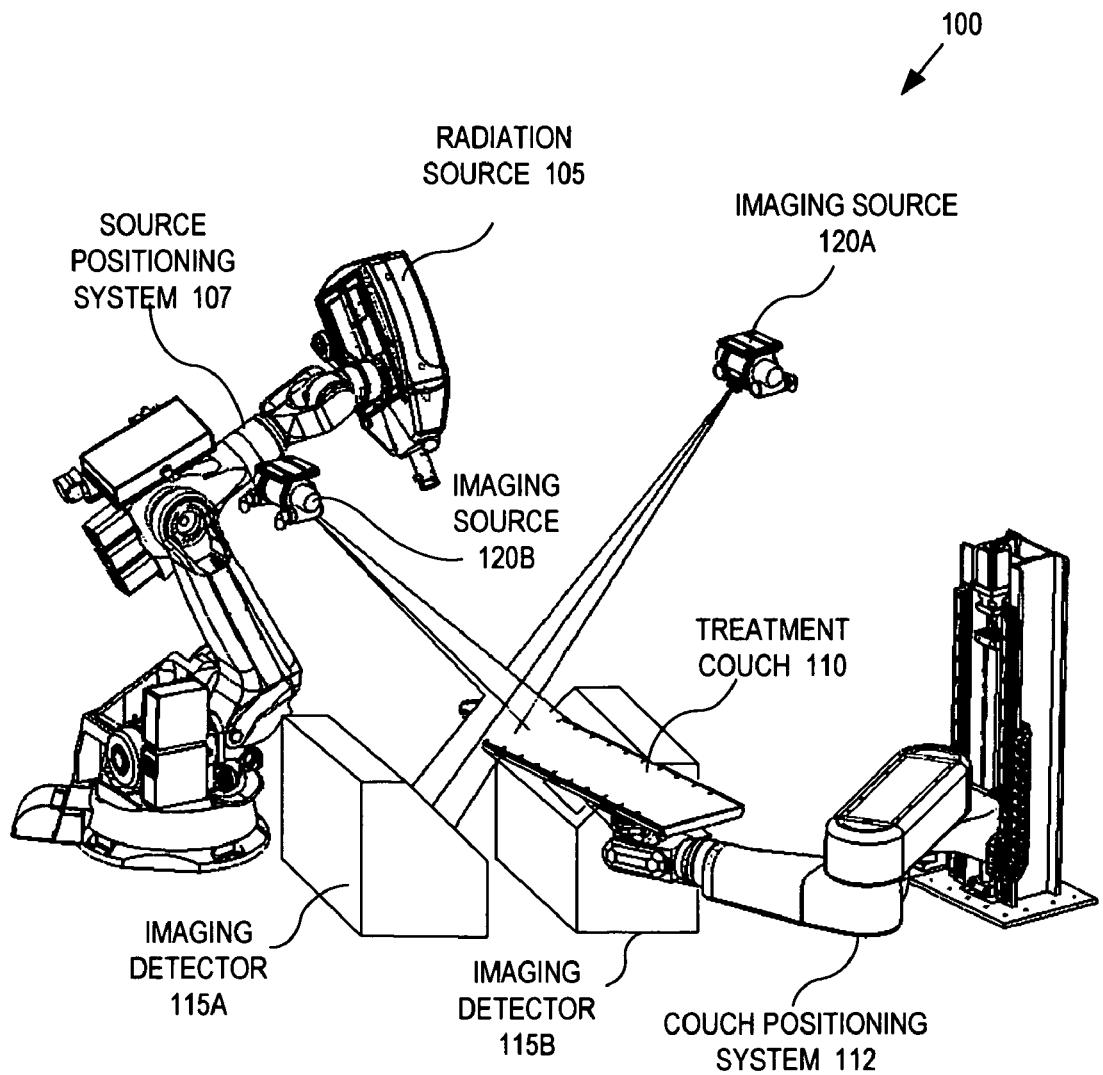
FIG. 7 is a perspective view of a radiation delivery system, in accordance with an embodiment of the invention.

FIG. 7 is a perspective view of a radiation delivery system 100, in accordance with an embodiment of the invention. In one embodiment, radiation delivery system 100 may be an image-guided, robotic-based radiation treatment system such as the CyberKnife® system developed by Accuray, Inc. of California. In FIG. 7, radiation source 105 may be a linear accelerator ("LINAC") mounted on the end of a source positioning system 3012 (e.g., robotic arm) having multiple (e.g., 5 or more) degrees of freedom in order to position the LINAC to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target). Treatment can be delivered in either a single session (mono-fraction) or in a small number of sessions (hypo-fractionation) as determined during treatment planning. With radiation delivery system 100, in one embodiment, radiation beams may be delivered according to the treatment plan without fixing the patient to a rigid, external frame to register the intra-operative position of the target volume with the position of the target volume during the pre-operative treatment planning phase.

Imaging system 3020 (see FIG. 6) may be represented by imaging sources 120A and 120B and imaging detectors (imagers) 115A and 115B in FIG. 7. In one embodiment, imaging sources 120A and 120B are X-ray sources. In one embodiment, for example, two imaging sources 120A and 120B may be nominally aligned to project imaging x-ray beams through a patient from two different angular positions (e.g., separated by 90 degrees, 45 degrees, etc.) and aimed through the patient on treatment couch 110 toward respective detectors 115A and 115B. In another embodiment, a single large imager can be used that would be illuminated by each x-ray imaging source. Alternatively, other numbers and configurations of imaging sources and detectors may be used.

Digital processing system 3030 may implement algorithms to register images obtained from imaging system 3020 with pre-operative treatment planning images in order to align the patient on the treatment couch 110 within the radiation delivery system 100, and to precisely position the radiation source 105 with respect to the target volume.

In the illustrated embodiment, treatment couch 110 is coupled to a couch positioning system 112 (e.g., robotic couch arm) having multiple (e.g., 5 or more) degrees of freedom. Couch positioning system 112 may have five rotational degrees of freedom and one substantially vertical, linear degree of freedom. Alternatively, couch positioning system 112 may have six rotational degrees of freedom and one substantially vertical, linear degree of freedom or at least four rotational degrees of freedom. Couch positioning system 112 may be vertically mounted to a column or wall, or horizontally mounted to pedestal, floor, or ceiling. Alternatively, the treatment couch 110 may be a component of another mechanical mechanism, such as the Axum™ treatment couch developed by Accuray, Inc. of California, or be another type of conventional treatment table known to those of ordinary skill in the art.

Alternatively, radiation delivery system 100 may be another type of treatment delivery system, for example, a gantry based (isocentric) intensity modulated radiotherapy ("IMRT") system or 3D conformal radiation treatments. In a gantry based system, a therapeutic radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A respiration phantom for performing quality assurance on a radiation delivery system, comprising:
   a human-like skeletal structure;
   at least one deformable component positionable at least partially internal to the human-like skeletal structure, the deformable component having a shape resembling an organ of a human anatomy, wherein the deformable component attenuates radiation substantially similarly to the organ of the human anatomy; and
   a respiration actuator positioned to deform the deformable component with a respiration-like motion.

2. The respiration phantom of claim 1, wherein the human-like skeletal structure is radiographically distinct, wherein the respiration phantom comprises an anthropomorphic phantom that radiographically images substantially similar to the human anatomy, and wherein the respiration phantom attenuates radiation substantially similar to the human anatomy.

3. The respiration phantom of claim 2, wherein the deformable component is removable from the skeletal structure.

4. The respiration phantom of claim 3, wherein the deformable component comprises a radiologically sensitive gel in a deformable container shaped to resemble the organ of the human anatomy.

5. The respiration phantom of claim 4, wherein the organ of the human anatomy comprises a lung and wherein the deformable container comprises a lung shaped container.

6. The respiration phantom of claim 3, wherein the human-like skeletal structure includes a rib cage and further comprising a plurality of deformable components positionable internal to the human-like skeletal structure, the plurality of deformable components each having a different shape resembling a different organ of the human anatomy, wherein the plurality of deformable components are removeable from the human-like skeletal structure and wherein the plurality of deformable components each attenuate radiation substantially similar to a corresponding organ of the human anatomy.

7. The respiration phantom of claim 6, further comprising:
   a thoracic cavity formed within the human-like skeletal structure; and
   a diaphragm positioned within the human-like skeletal structure, wherein the respiration actuator is coupled to move the diaphragm along an inferior to superior axis and wherein the thoracic cavity is flexible to expand along a posterior to anterior axis in response to motion from the diaphragm.

8. The respiration phantom of claim 6, further comprising a skin-like sheath surrounding the human-like skeletal structure.

9. The respiration phantom of claim 6, wherein the plurality of deformable components comprise foam organs, and wherein each of the plurality of deformable components are each individually removable and replaceable with a radiologically sensitive gel organ.

10. The respiration phantom of claim 6, wherein the respiration actuator comprises a mechanical actuator coupled to reciprocally compress the plurality of deformable components along an inferior to superior axis and to cause the rib cage to expand along a posterior to anterior axis.

11. The respiration phantom of claim 6, wherein the respiration actuator comprises a pneumatic actuator coupled to reciprocally compress the plurality of deformable components along an inferior to superior axis and to cause the rib cage to expand along a posterior to anterior axis.

12. The respiration phantom of claim 1, wherein the respiration actuator is programmable to simulate multiple different respiration-like motions.

13. A system, comprising:
   a respiration phantom comprising:
      a human-like skeletal structure;
      at least one deformable component positionable at least partially internal to the human-like skeletal structure, the deformable component having a shape resembling an organ of a human anatomy, wherein the deformable component attenuates radiation substantially similarly to the organ of the human anatomy; and a respiration actuator positioned to deform the deformable component with a respiration-like motion; and a radiation delivery system including a radiation source and a patient positioning system, the patient positioning system to position the respiration phantom at a preset position and the radiation source moveable to deliver a dose of radiation to the respiration phantom while the respiration actuator is deforming the deformable component with the respiration-like motion.

14. The system of claim 13, wherein the radiation delivery system comprises an image guided radiation delivery system, wherein the image guided radiation delivery system further includes an imaging system to image the respiration phantom and provide real-time feedback to align the radiation source during delivery of the dose of radiation.

15. The respiration phantom of claim 14, wherein the human-like skeletal structure is radiographically distinct, wherein the respiration phantom comprises an anthropomorphic phantom that radiographically images substantially similar to the human anatomy, and wherein the respiration phantom attenuates radiation substantially similar to the human anatomy.

16. The system of claim 15 wherein the respiration phantom includes a sensor array within the human-like skeletal structure to determine whether the dose of radiation was delivered to the respiration phantom as expected.

17. The system of claim 15, wherein the deformable component is removable from the skeletal structure for analysis to determine whether the dose of radiation was delivered to the deformable component as expected.

18. The system of claim 17, wherein the deformable component comprises a radiologically sensitive gel in a deformable container shaped to resemble the organ of the human anatomy.

19. The system of claim 17, wherein the human-like skeletal structure includes a rib cage and further comprises a plurality of components positionable internal to the human-like skeletal structure, the plurality of components each having a different shape resembling a different organ of the human anatomy, wherein the plurality of components are removeable from the human-like skeletal structure and wherein the plurality of components each attenuate radiation substantially similar to a corresponding organ of the human anatomy.

20. The system of claim 19, wherein the respiration actuator is coupled to reciprocally compress the plurality of components along an inferior to superior axis and to cause the rib cage to expand along a posterior to anterior axis.

21. A respiration phantom for performing quality assurance on a radiation delivery system, comprising:

means for providing a human-like skeletal structure;

means for attenuating radiation substantially similar to a organ of a human anatomy, the means for attenuating positioned internal to the means for providing a human-like skeletal structure, the means for attenuating having a shape resembling the organ of a human anatomy and being deformable; and actuator means for deforming the means for attenuating with a respiration-like motion.

22. The respiration phantom of claim 21, wherein the means for providing a human-like skeletal structure is radiographically distinct, wherein the respiration phantom comprises an anthropomorphic phantom that radiographically images substantially similar to the human anatomy, and wherein the respiration phantom attenuates radiation substantially similar to the human anatomy.

23. The respiration phantom of claim 22, wherein the means for attenuating is removable from the means for providing a human-like skeletal structure.

24. The respiration phantom of claim 23, wherein the means for attenuating comprises a radiologically sensitive gel in a deformable container shaped to resemble the organ of the human anatomy.

25. The respiration phantom of claim 22, further comprising a plurality of means for attenuating positionable internal to the means for providing the human-like skeletal structure, the plurality of means for attenuating each having a different shape resembling a different organ of the human anatomy, wherein the plurality of means for attenuating are removeable from the means for providing the human-like skeletal structure and wherein the plurality of means for attenuating each attenuate radiation substantially similar to a corresponding organ of the human anatomy.

26. The respiration phantom of claim 25, wherein the actuator means comprises a means to reciprocally compress the plurality of means for attenuating along an inferior to superior axis of the respiration phantom and to cause the means for providing the human-like skeletal structure to expand along a posterior to anterior axis of the respiration phantom.

27. A method of performing quality assurance on a radiation delivery system, comprising:

cyclically compressing a deformable component internal to a respiration phantom having a human-like skeletal structure along an inferior to superior axis of the respiration phantom, the deformable component having a shape resembling an organ of a human anatomy, wherein the cyclical compression causes the human-like skeletal structure to cyclically expand along a posterior to anterior axis of the respiration phantom; and emitting a radiation beam from a radiation source of the radiation delivery system at the respiration phantom while cyclically compressing the deformable component.

28. The method of claim 27, further comprising analyzing a dose of radiation delivered to the respiration phantom to determine whether the radiation delivery system is calibrated.

29. The method of claim 27, further comprising positioning the respiration phantom at a preset position with a robotic couch positioning system.

30. The method of claim 29, wherein positioning the respiration phantom comprises positioning the respiration phantom under feedback guidance of a radiation image guidance subsystem of the radiation delivery system.

31. The method of claim 30, wherein the human-like skeletal structure is radiographically distinct, wherein the respiration phantom comprises an anthropomorphic phantom that radiographically images substantially similar to the human anatomy, and wherein the respiration phantom attenuates radiation substantially similar to the human anatomy.

32. The method of claim 27, wherein emitting the radiation beam at the respiration phantom comprises emitting the radiation beam at the deformable component, and further comprising:

removing the deformable component from the respiration phantom, wherein analyzing the dose of radiation delivered to the respiration phantom comprises analyzing the dose of radiation delivered to the deformable component to determine whether the radiation delivery system is calibrated.

33. The method of claim 32, wherein the deformable component comprises a radiologically sensitive gel in a deformable container shaped to resemble the organ of the human anatomy.

* * * * *